United States Patent
Joensuu et al.

(10) Patent No.: US 12,043,559 B2
(45) Date of Patent: Jul. 23, 2024

(54) METHOD AND SYSTEM FOR MONITORING PROPERTIES OF AN AQUEOUS STREAM

(75) Inventors: Iiris Joensuu, Espoo (FI); Marjatta Piironen, Oulu (FI); Eija Saari, Espoo (FI); Jukka-Pekka Sirviö, Espoo (FI); Seppo Tuomivaara, Kiviniemi (FI)

(73) Assignee: KEMIRA OYJ, Helsinki (FI)

( * ) Notice: Subject to any disclaimer, the term of this patent is extended or adjusted under 35 U.S.C. 154(b) by 0 days.

(21) Appl. No.: 13/811,072

(22) PCT Filed: Jul. 19, 2011

(86) PCT No.: PCT/FI2011/050667
§ 371 (c)(1),
(2), (4) Date: Apr. 1, 2013

(87) PCT Pub. No.: WO2012/010745
PCT Pub. Date: Jan. 26, 2012

(65) Prior Publication Data
US 2013/0220922 A1    Aug. 29, 2013

(30) Foreign Application Priority Data
Jul. 20, 2010    (FI) .................................. 20105813

(51) Int. Cl.
*C02F 1/52*     (2023.01)
*B01D 21/01*    (2006.01)
(Continued)

(52) U.S. Cl.
CPC ............ *C02F 1/5209* (2013.01); *B01D 21/01* (2013.01); *B01D 21/32* (2013.01); *G01N 33/343* (2013.01);
(Continued)

(58) Field of Classification Search
CPC ................ C02F 1/5209; C02F 2209/11; C02F 2209/001; C02F 2103/28
See application file for complete search history.

(56) References Cited

U.S. PATENT DOCUMENTS

| | | | |
|---|---|---|---|
| 4,194,391 | A | 3/1980 | Rosenberger |
| 4,279,759 | A | 7/1981 | Pardikes |

(Continued)

FOREIGN PATENT DOCUMENTS

| | | |
|---|---|---|
| BR | 112013001498-9 A2 | 1/2012 |
| CH | 516 329 | 12/1971 |

(Continued)

OTHER PUBLICATIONS

Sigrist On-Line Turbidimeter WTM2500, Sep. 2000, 4 pages.*
(Continued)

*Primary Examiner* — Chester T Barry
(74) *Attorney, Agent, or Firm* — Espatent Oy

(57) ABSTRACT

The invention concerns an online method and system for monitoring properties of an aqueous stream of an industrial process. The method comprises providing an initial aqueous stream originating from said process, the aqueous stream containing solid matter exhibiting a first settling behavior; adding modifying agent to the initial aqueous stream at an addition rate sufficient to provide a modified aqueous stream containing solid matter exhibiting a second settling behavior different from the first settling behavior; conducting a sample of the initial aqueous stream or modified aqueous stream, any combination stream comprising the modified aqueous stream or any substream of the modified aqueous stream batchwise from a sampling point to a settling vessel having a volume; and measuring the settling behavior of the solid matter in the sample locally in the settling vessel as a function of time. The invention can be used for efficient monitoring and, optionally, controlling the degree of
(Continued)

agglomeration of pulp and paper or board manufacturing processes.

18 Claims, 3 Drawing Sheets

(51) Int. Cl.
    *B01D 21/32*      (2006.01)
    *C02F 103/28*      (2006.01)
    *G01N 33/34*      (2006.01)

(52) U.S. Cl.
    CPC .... *C02F 2103/28* (2013.01); *C02F 2209/001* (2013.01); *C02F 2209/11* (2013.01)

(56) References Cited

U.S. PATENT DOCUMENTS

| | | | | |
|---|---|---|---|---|
| 4,544,840 A * | 10/1985 | Keller | ............... | G01F 23/292 |
| | | | | 250/227.23 |
| 5,001,938 A | 3/1991 | Downie | | |
| 5,620,609 A * | 4/1997 | Field | ............... | C02F 1/5209 |
| | | | | 210/198.1 |
| 5,645,799 A | 7/1997 | Shah et al. | | |
| 5,809,825 A | 9/1998 | Howard | | |
| 6,649,068 B2 * | 11/2003 | Phillips | ............... | 210/739 |
| 2004/0182138 A1 * | 9/2004 | Greenwood | ........... | G01N 15/04 |
| | | | | 73/53.03 |
| 2008/0047903 A1 * | 2/2008 | Morse | ............... | B01F 3/0446 |
| | | | | 210/704 |
| 2009/0255876 A1 * | 10/2009 | Dunbar | ............... | C02F 1/008 |
| | | | | 210/709 |
| 2011/0067832 A1 * | 3/2011 | Xia | ............... | D21H 21/36 |
| | | | | 162/100 |
| 2011/0155255 A1 * | 6/2011 | Ladron de Guevara | ........... | |
| | | | | C02F 1/5209 |
| | | | | 137/3 |
| 2013/0120556 A1 * | 5/2013 | Dorris | ............... | G06K 9/78 |
| | | | | 348/92 |
| 2013/0153510 A1 | 6/2013 | Jansson et al. | | |
| 2013/0335731 A1 * | 12/2013 | Jorden | ............... | 356/73 |

FOREIGN PATENT DOCUMENTS

| | | | | |
|---|---|---|---|---|
| CH | 516329 | * | 12/1971 | ............ B01D 21/01 |
| GB | 2 050 336 A | | 1/1981 | |
| JP | 2007-57516 A | | 3/2007 | |
| WO | WO 94/17394 A1 | | 8/1994 | |
| WO | WO 99/14591 A1 | | 3/1999 | |
| WO | WO 00/43322 A1 | | 7/2000 | |
| WO | WO 2004/057306 A1 | | 7/2004 | |

OTHER PUBLICATIONS

Hach 1720E Low Range Turbidimeter, May 2007, Edition 7, 39 pages.*
Valmatic Air in Pipelines Sources, System Impact and Removal, 1993, 12 pages.*
USGS, Monitoring Instream Turbidity to Estimate Continuous Suspended-Sediment Loads and Yields and Clay-Water Volumes in the Upper North Santiam River Basin, Oregon; p. 18-21 (Year: 2003).*
Edler, Clarification of Turbidity Requirements for Filtered Systems under the Surface Water Treatment Rule (SWTR), Feb. 1, 1994, p. 1-4 (Year: 1994).*
AS Automation Solutions, "Red-Tech," Information Sheet, http://asautosol.co.za/files/content/docs/redtech_brochure.pdf, Downloaded from the Internet in Jun. 2011, 1 page.
European Office Communication for European Application No. 11770832.1, dated Jun. 28, 2016.
Mantovanelli et al., "Devices to measure settling velocities of cohesive sediment aggregates: A review of the in situ technology," Journal of Sea Research, vol. 56, 2006 (Available online Jun. 17, 2006), pp. 199-226.
McClements, "Ultrasonic Measurements in Particle Size Analysis," Encyclopedia of Analytical Chemistry, Sep. 15, 2006, pp. 1-8.
Brazilian Office Action for Brazilian Application No. BR112013001498-9, dated Dec. 5, 2019, with English translation.
Brazilian Office Action for Brazilian Application No. BR112013001501-2, dated Dec. 5, 2019, with English translation.
Finnish Search Report issued in 20105813 dated Apr. 5, 2011.
International Search Report issued in PCT/FI2011/050667, dated Nov. 22, 2011.

* cited by examiner

METHOD AND SYSTEM FOR MONITORING PROPERTIES OF AN AQUEOUS STREAM

BACKGROUND OF THE INVENTION

1. Field of the Invention

The present invention relates to treatment of aqueous streams. In particular, the present invention concerns method and system of monitoring properties of an aqueous stream in an industrial process, in particular in a pulping process or paper or board manufacturing process. The method comprises providing an aqueous stream originating from said process, the aqueous stream containing solid matter exhibiting a first settling behavior and adding modifying agent to the aqueous stream to provide a modified aqueous stream having solid matter exhibiting a second settling behavior different from the first settling behavior. The solid matter may be in the aqueous stream in suspended and/or colloidal form and/or dissolved matter which may be precipitated.

2. Description of Related Art

Examples of aqueous streams containing significant amounts of solid matter and/or dissolved matter which may be precipitated, include industrial flows for example streams in the pulp and papermaking processes. The flows may comprise for example thin and thick stock of a paper/board making process and water streams. Aqueous streams in pulp and papermaking processes contain variable amounts of fiber material. Depending on the origin of the aqueous stream, other solid matter can be organic or inorganic or a combination thereof. There may also be included some biological matter. The solid matter concentration, including precipitable dissolved matter, can vary broadly. Typically, it ranges from about 0.1 to 30% by weight of the aqueous flow.

Common for many streams of the above kind is that there is a need to regulate the settling properties of solid matter present in suspended, colloidal and/or precipitable form in the water. In the following all of these types of matter will be referred to as "solid matter". Modifying agents, such as coagulants, flocculants, passivating chemicals, surfactants, dispersing agents, retention aids, microparticles, sizing agents and/or enzymes are typically used for said regulation.

As a concrete example, in many streams of a pulping process or a paper and board manufacturing process there is a need to control the amount, size and/or nature of solid matter present in the aqueous stream. One important target of chemistry management is to maintain good and even attachment of particles to the fibers and/or fiber web and thereby to prevent the accumulation of solid matter in the aqueous streams. However, a part of solid matter typically remains unattached to the fibres when the pulp suspension is fed onto the wire, or when the fiber web is formed on the wire. Therefore variable amounts of the solid matter enters paper machine water system. This solid matter typically contains inorganic, organic and biological material originating from the raw water, recycled water, fibers and coated broke, e.g. natural and white pitch, stickies, tackies, microbes, pigments and binder(s) and additives. It is then desired to keep the remaining solid matter evenly dispersed in water to prevent its agglomeration or uncontrolled agglomeration since this will result in increased deposition and consequent effect on machine runnability and product quality.

Apart from agglomeration of particles in aqueous streams which contain less fibers, such as white water of the paper machine, agglomeration of particles can take place also in pulp flows having higher fiber concentrations in pipelines, or in tanks in pulp mill and paper machine, or in broke, or in preparation or different kinds of pulps, e.g. chemical, chemi-mechanical or mechanical pulp. Often agglomeration of particles is caused by improper management of process chemistry e.g. inadequate dosing or overdosing of modifying agent(s) or unsuited chemistry. Uncontrolled interaction between the solid matter particles and/or fibers often results in agglomeration causing a significant drop in number of particles.

Agglomerating particles and agglomerates may be hydrophobic or hydrophilic or a combination thereof. The amount of microbes in the suspension may also be high: up to 10 million/ml or more, which also contributes to the agglomeration.

When the size of the particles in the system is small enough they usually do not adversely affect the runnability of the papermaking process or the quality of the paper. Allowable size depends on the process and equipment used. However, increase in particle size usually generates problems. For example, agglomeration of solid matter may lead to fast settling of the solid matter and consequent deposition on equipment surfaces. Often hydrophobic particles are more troublesome in the process. Deposit formation also fouls e.g. wires and felts thereby impairing the runnability of the papermaking process. Agglomeration also deteriorates even bonding of the particles to the fibres, and consequently the defects in the paper become more visible.

Thus, it is preferred to have the solid matter in the process in a desired size and/or count and/or with desired surface properties. This can be achieved by controlling the amount of modifying chemicals, such as fixatives, in the process stream.

Thus, typically, modifying agent(s) is/are added at one or several addition point(s) to the aqueous stream at an addition rate estimated to be sufficient to change the surface properties and/or agglomeration tendency of the particles in the process streams. However, a problem of determining the required amount and/or type(s) of modifying chemical(s) arises.

The performance of the modifying chemicals is normally analyzed on basis of simple laboratory tests like turbidity and cationic demand. The result obtained is a sum of different reactions and does not describe e.g. changes in particle size. Sophisticated laboratory methods are available, but they usually involve many sample preparation steps and are thus very complicated and time consuming. However, the mentioned laboratory methods represent quality of the process streams only at a one time point.

Known devices for measuring settling velocities of cohesive sediment aggregates are discussed in A. Mantovanelli, P. V. Ridd, *Journal of Sea Research* 56 (2006) 199-226. These include hand-operated settling tubes and automated settling columns equipped with video systems, optical and laser instruments and an underwater balance.

Another problem is that, rapid quality changes often exist in aqueous process streams. On the other hand, delays in process due to circulating streams and long circulation cycles may be long, even days. This results in temporary over- or under-dosing of modifying agents with consequent effects on paper quality (e.g. more defects in paper due to deposits) and economy of the process.

Only a few online measurements for monitoring the aqueous streams, and optionally controlling the dosing exist.

U.S. Pat. No. 4,279,759 discloses one method for controlling the feed rate of water treatment chemicals to a process stream. In the method, a sample stream is obtained as a side stream of the process stream and fed with constant rate to a settling column, in which the concentration of solids is determined continuously. The method requires a continuous stream to be fed through the settling column at a suitable feed rate. Thus, although the method aids in online monitoring, its capability to determine settling properties of the sample is quite limited.

US 2004/0182138 discloses a method for ultrasonic characterization of settling suspensions. The method is based on determining a peak time measurement of consistency of samples. The method is best suitable for high-consistency samples (>10% by weight) and for pre-characterized samples comprising particles of essentially one size only (monodisperse samples). For lower consistencies and polydisperse samples, the peak time measurement is expected to give inferior results due to reduced sensitivity. A further drawback of ultrasonic characterization is that the sound waves have an effect on the temperature and oscillations in the sample which may influence its settling properties.

Therefore, there is a need for on-line monitoring system in order to be able to change in time chemical dosing rates and/or selection of chemicals used when the quality of the streams changes. In particular, there is a need in industrial processes for methods for on-line monitoring of and/or controlling chemical dosing to aqueous flows containing solid matter. Such need exists in particular when monitoring process streams for the effect of chemicals affecting particle size, agglomeration and/or particle interactions of the solid matter. In addition there is a need for a method for controlling dosing of modifying agents affecting particle size, agglomeration and/or particle interactions of the solid matter or particle size management of solid matter in the process. Of specific interests herein are processes in which the process streams have long circulation or throughput times, whereby also delays in process monitoring and/or controlling can be very long. Thus, there is a need for reduced-delay monitoring and/or controlling methods.

SUMMARY OF THE INVENTION

It is an aim of the present invention to eliminate at least a part of the problems relating to the known art and to provide an improved method and system for online monitoring of properties of aqueous streams of an industrial process, such as a circulation streams in a paper or board manufacturing process.

In particular, it is an aim of the invention to provide a method and system for online monitoring of the settling behavior of solid matter of an aqueous process stream and optionally for regulating chemical addition to affect the settling behavior of the solid matter in the stream.

It is a further aim to provide means for estimating and, optionally reducing the agglomeration risk in an aqueous process stream of a paper machine.

The present invention is based on the idea of determining a local change of settling behavior of solid particles in small samples taken from the bulk of aqueous stream before and/or after addition of modifying chemical(s); based on the settling behavior of the sample, conclusions can be drawn regarding the bulk large flow. The determination may be performed by measurement, preferably batchwise and sequentially in repeating cycles.

The method according to the invention allows monitoring of the aqueous flows by frequent and fast measurements describing settling behavior of the solid matter in the streams. The measurement used may even be used to describe or evaluate the mean particle size of the sample. The method may even be more informative concerning the quality of the aqueous stream representing state of the process compared e.g. with sole particle size measurements, since particle size measurements often exclude important factors affecting settling behavior, such as e.g. particle shape and density.

The quantity of interest determined from the sample can be, for example, settling velocity of the solid particles. Depending on the process and characteristics of solid matter, correlation between measured settling behavior, e.g. settling velocity, mean particle size and/or hydrophobic particle size can be derived.

Therefore, present invention comprises the steps of
providing an initial (first) aqueous stream originating from an industrial process, the initial aqueous stream containing solid matter in suspended and/or colloidal and/or precipitable form, the solid matter exhibiting a first settling behavior;
adding modifying agent(s), such as cationic chemicals, to the initial aqueous stream to provide a modified (second) aqueous stream containing solid matter exhibiting a second settling behavior different from the first settling behavior;
conducting a sample of the initial or modified aqueous stream, any combination stream comprising the modified aqueous stream or any substream of the modified aqueous stream, from a sampling point to a settling vessel having a volume; and
allowing the sample to settle in the settling vessel and simultaneously measuring the settling behavior of the solid matter in the sample locally in the settling vessel as a function of time.

Optionally, depending on the determined settling velocity, the addition rate of the modifying agent added to the initial aqueous stream is controlled. In addition to or instead of addition rate, the type of the modifying agent can be controlled.

Preferably, the measurement of the settling behavior of the sample comprises at least one of the following: measuring the solid matter content of the sample, measuring the turbidity of the sample, measuring the amount of suspended solids in the sample or measuring the consistency of the sample.

Based on the temporal settling behavior of the solid matter, one can determine e.g. one or more of the following: the settling velocity of the solid matter in the sample, the settling time of the solid matter in the sample, or the time required for the sample to reach a predetermined turbidity value.

According to an advantageous embodiment, the settling velocity of the solid matter in the sample is determined based on the measurement. The settling velocity depends on changes as a function of time. This may be correlated with mean particle size of the sample. Thus, information from the particle size is obtained.

The settling velocity can be determined as turbidity per time unit (e.g. NTU/s) or as other quantity indicative of solid matter settling in the sample per time unit, e.g. amount of solid matter per time unit.

According to one embodiment, the method comprises measuring the solid matter content or turbidity of the sample or the amount of suspended solids or consistency in the sample as a function of time, and based on said measurement, determining the settling velocity or the settling time of the solid matter in the sample or the time required for the sample to reach a predetermined turbidity value. Further said measurements are carried out at a first temporal settling region during which the turbidity of the sample is at least 20% higher than the turbidity at end of settling cycle. During this region, the sample is allowed to settle unperturbed. According to one embodiment, the settling velocity of the sample is determined at least at one moment of time or over a time span by calculating a time derivative of said measurement or slope between at least two moments of time in said first settling region. Consequently, the settling velocity can be reliably determined.

According to one embodiment, the settled turbidity of the sample is measured after the measurement of the settling velocity, typically at a second temporal settling region during which the turbidity is less than 50% higher than turbidity at end of settling cycle. The settling velocity and settled turbidity characterize the stream in many cases well and provide additional information for improved process control.

Typically, the settling velocity at the first settling region is at least twofold compared with the settling velocity at the second settling region.

The present method is suitably applied in some preferred embodiments for aqueous streams, preferably polydisperse, whose consistency is 5% by weight or less or 2% by weight or less. The present method is most suitably applied for polydisperse aqueous streams whose consistency is 1% by weight or less.

Local measurement of the solid matter content of the sample is beneficial as the solid matter content generally obeys the formula f(x,y,z,t), where x,y are horizontal and z vertical spatial coordinates within the settling vessel and t is time. "Local" in this context means that measurement data is collected only from a certain region in the settling vessel (in the vicinity of a sensor head used), the volume of the region being smaller than the volume of the settling vessel. Preferably, the measurement is performed substantially at the same location with reference to the direction of the vertical axis of the settling vessel. Measurement of the settling behavior as a function of time means that the measurement is carried out at least at two different time points. For example the solid matter content or turbidity of the sample is measured at at least two time points. Mathematical transformation of the measured data or a part thereof, e.g. logarithm or derivative and/or slope can be utilized for determining parameters describing settling behavior of the solid matter. In addition, based on the measurements as a function of time, a separate value or values of each of the data sequential measurements may be used for monitoring purposes.

The selectivity of the present method for the particles concerned is affected, for example, by the time span of the measurement, measurement location, and by specifications of the measurement device used (such as radiation wavelength of an optical or microwave detector).

In particular, the settling velocity of the solid matter in the sample, which is not constant over time due to the fact that the sample contains a distribution of particles with different sizes and settling properties, is determined in the beginning phase of the settling process. The sample in the settling vessel exhibits a first temporal settling region of first settling velocity (dominated by solid particles having a size larger than the average size of said solid matter in the sample) and a second temporal settling region of second settling velocity smaller than the first settling velocity (dominated by solid particles having a size smaller than the average size of said solid matter). The measurement of settling behavior is preferably carried out in the first temporal settling region. By such arrangement, information is obtained regarding the largest particles which are probably most detrimental to the industrial process concerned. Typically, the settling velocity is determined during the first settling region of the settling cycle. In particular, the settling velocity is determined during the first half of the settling cycle, which, in practice often means the first 180 seconds of the settling cycle.

It should be noted that the modifying agent can be added to the aqueous stream in a very different stage of the process compared to the stage where the sample is taken from. Thus, the stream can be treated in any chemical, mechanical or physical way between these stages. Alternatively or in addition to that, the stream may be combined with any other process stream and/or divided into a smaller substream between these stages.

For example, in a paper or board manufacturing process, the aqueous stream to which the modifying agent is added can be a broke stream, a chemical pulp stream, a mechanical pulp stream, a chemi-mechanical pulp stream, a recycled pulp stream, white water stream or another internal circulation water stream, and the sampling can be carried out at any of their combination streams or a substream divided from the initial stream or combination stream. The modifying agents can also be added during or before the preparation of the pulps.

Moreover, the same or some other type of modifying agent(s) can additionally be added at intermediate stages between the initial addition point and the sampling point.

According to one embodiment, the sample is taken from an aqueous circulation stream, e.g. white water or wire water in a paper or board machine which is used for diluting thick pulp fed into the headbox of the paper or board machine. The stream is finally circulated to the headbox of the paper or board machine. In such a stream, as well as other streams the invention can be applied to, the solid matter may comprise inorganic pigments, fillers and/or precipitates, organic compounds and polymers and biological matter and combinations thereof, in particular pitch, latex, stickies or a combination thereof.

As discussed above, the present method is most suitable for relatively low-consistency streams. However, the sample can also be taken from an aqueous stream containing variable, also high, amounts of solid matter. If the sample is taken from a stream containing a high amount of fibres, the sample is preferably filtered and/or screened in order to obtain a substantially fiber-free sample from which the solid matter content is easier to measure. After filtration or screening, the consistency is preferably 5% by weight or less, in particular 2% by weight or less, most suitably 1% by weight or less.

In a preferred embodiment, more than 50% by weight of solid matter in the filtered sample consists of non-fibrous solid matter.

Considerable advantages are obtainable by the invention. Thus, generally, the settling velocity is an efficient parameter for controlling feed and/or type of modification agent(s). When the largest particles in the stream are of interest, the measurement can be carried out very quickly in the beginning of the settling cycle and agglomeration can be predicted without excessive delays.

Batchwise sampling and measurement where the sample is allowed to settle unperturbed allows one to assess both the small and large particles in the sample, in contrast to prior art methods where the sample flow is continuous or the sample is mixed during measurement. In this invention too, the measurement may be continuous during each settling cycle in order to obtain temporal and particle-size dependent information on settling, but the sample is not a continuous flow but a representative batch of an initial process stream, whose behavior is then measured. Indeed, in some embodiments of the invention data is obtained from at least two temporal regions of settling which are dominated by particles of different sizes. This allows for enhanced process control, including chemistry control. Chemistry control may include selection of suitable modifying chemical(s) and or control of the amount and/or addition point(s) of the chemical(s).

By controlling the solid matter concentration in aqueous streams of pulp and papermaking processes, with correct amounts of modifying agent(s), agglomeration of particles can be regulated and there are less detrimental effects on the production, e.g. fewer defects in paper or deposits on machine surfaces.

Next the invention will be examined more closely with the aid of a detailed description and with reference to the attached drawings.

DETAILED DESCRIPTION OF EMBODIMENTS

Figure 1A:
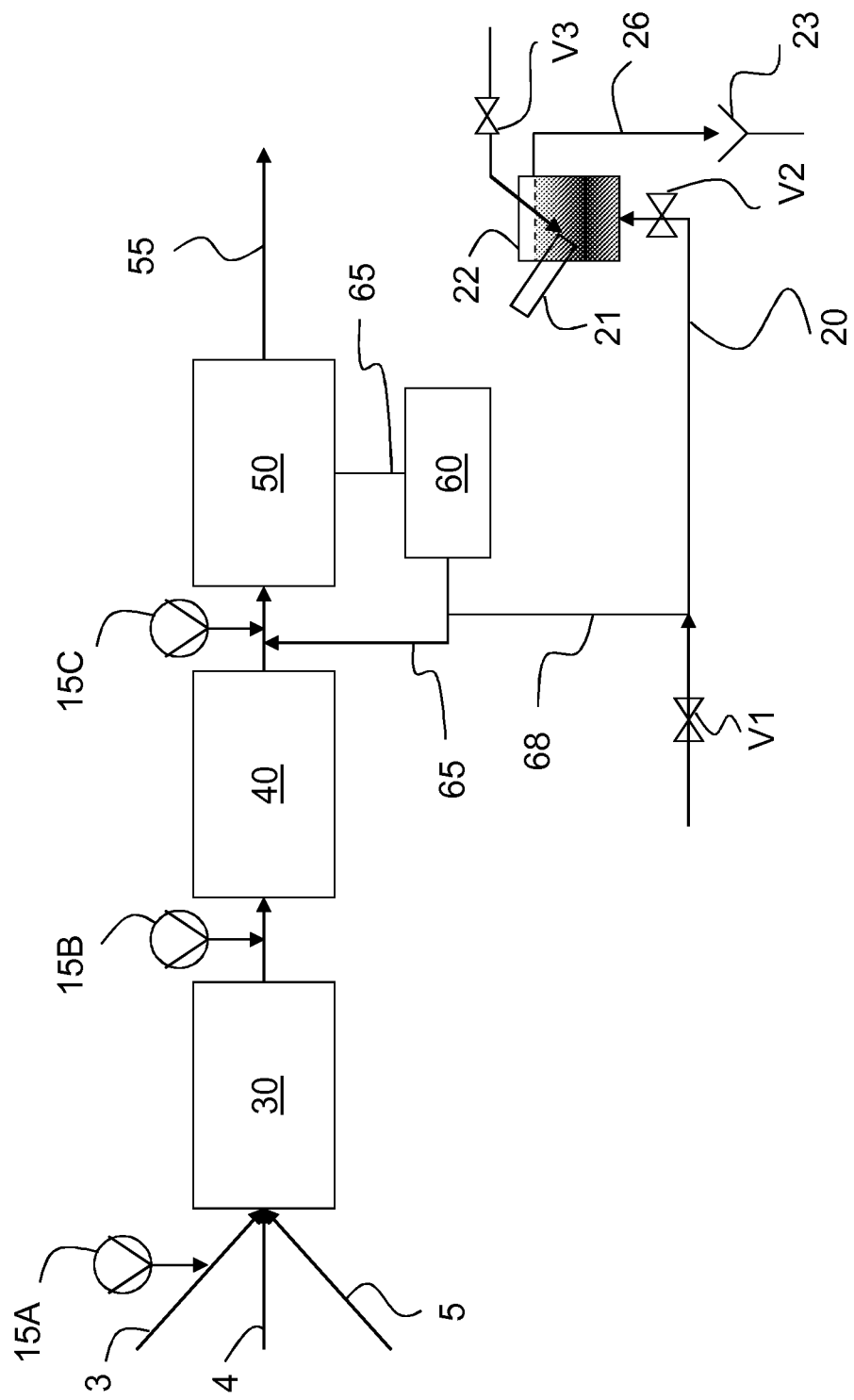
FIG. 1a shows a paper making process with a sampling sidestream according to one embodiment of the invention.

As was discussed above, the present invention comprises basically a method of treating an initial aqueous stream with at least one modifying agent to obtain a modified aqueous stream. The modified aqueous stream has modified settling properties. According to a preferred embodiment, a sample is withdrawn from the modified aqueous stream and based on the sample, the settling velocity of the modified aqueous stream is determined in a settling vessel.

In the description and claims, the term "initial aqueous stream" refers to any stream in the process which is treated with a modifying agent. The term "modified aqueous stream" is not restricted only to the initial aqueous stream immediately after treatment with the modifying agent, but covers also streams treated in other ways, combined with one or several streams or divided into one or more substreams. Naturally, the modifying agent affects the settling behavior of not only of the treated aqueous stream but also combined streams and substreams the streams treated with the modifying agent or agglomerates affected by the modifying agent are conducted to. The invention also covers processes where more than one modifying agents are added to the process at one or more addition points or where the same modifying agent is added at several addition points.

According to one embodiment, the sampling is carried out before the addition of the modifying agent, i.e. from the initial aqueous stream. This is useful for making, predictive or feed forward control of the process in particular if the characteristics of the process are well known. Based on the settling behavior of the initial stream, demand of modifying agent can be estimated. However, in most cases the sampling is carried out only after addition of the modifying agent, which ensures that real settling behavior is observed and the demand and/or type of the modifying agent can be more accurately determined and preferably controlled. Settling behavior of the modified stream is controlled feed back by modifying agents.

According to a preferred embodiment, depending on the determined settling behavior in the settling vessel, the addition rate and/or type of the modifying agent is changed. It is possible to use soft sensors and models [e.g. Linguistic Equation (LE)] to assist in data interpretation and justification. Other commercially available methods and devices, such as flow cytometer, can also be utilized in estimation and calculation. As regards suitable equipment we refer to the method and apparatus for automatic dose control of chemicals, described in WO 2005/022278, the contents of which are herewith incorporated by reference.

The present invention also comprises a solution wherein determination of the settling behavior is merely carried out as a monitoring step.

According to one embodiment, the invention is used for remote monitoring and/or control of the industrial process. Thus, the present measurement apparatus can be functionally connected with data transfer means capable of transferring the measurement data to a remote location and/or control data from the remote location to the location of the present industrial process. This is an important possibility and a significant advantage compared with prior art methods which typically require laboratory analysis and steps which must be carried out manually.

As discussed above, the settling velocity at a predetermined moment of time or time span is a preferred quantity to be determined from the sample. This is because the settling velocity or changes in the settling velocity correlate with particle size characteristics of the sample and is thus indicative of the degree of agglomeration of particles in paper, board and pulp processes.

The present invention also comprises a solution wherein, in addition to determining the settling velocity of the sample, a settled turbidity of the sample is determined and optionally used for changing the addition rate of the modifying agent. "Settled turbidity" means the turbidity after a predetermined time period, which is typically longer than the time period over which the settling velocity is determined. Typically, the time period before turbidity measurement is 5 minutes or more, in particular 10 minutes or more, whereas the settling velocity is measured before the expiry of this time period. Settled turbidity can also be a turbidity value which is not changing markedly any more (i.e. less than a predefined absolute or relative amount) by increased settling time.

According to one embodiment, the modifying agent is capable of affecting the surface properties and/or interaction between particles or between particles and fibers or other components in the stream. In some cases, a modifying agent is capable of agglomerating solid matter present in the aqueous stream.

According to a preferred embodiment of the invention, the modifying agent is selected from coagulants and/or flocculants. The coagulant or flocculant comprises or can be selected from salts or anionic, nonionic and cationic polyelectrolytes of uni- or multivalent cations, such as sodium, calcium, magnesium, iron, aluminum, natural products such as starch, semi-synthetic polymers such as cationic starch and synthetic polymers such as acrylic polymers, polyamines, polyethylene oxides and allylic polymers, or mixtures thereof.

Coagulation is destabilization of colloidal particles brought about by the addition of a chemical reagent known as a coagulant. Fine particles in a suspension collide with each other and stick together. Usually the particles are brought near to each other by Brownian motion or by flow (Water Treatment Handbook, Vol 1 and Vol 2, 1991, Degremont). Coagulant is typically an inorganic (anion/cation) or organic (polyelectrolyte) chemical, which neutralizes the negative or positive surface charge (destabilization) of the impurities, such as colloidal particles. (Water Treatment Handbook, Vol 1 and Vol 2, 1991, Degremont)

Flocculation refers e.g. to the action of polymers in forming bridges between suspended particles or working by patch models. A flocculant may promote the formation of the floc. Flocculant may be an inorganic polymer (such as activated silica), a natural polymer (starch, alginate) or synthetic polymers (Water Treatment Handbook, Vol 1 and Vol 2, 1991, Degremont, Water Quality and Treatment, A Handbook of Community Water Supplies).

Alternatively or additionally, the modifying agent can be typically be passivating chemicals, surfactants, dispersing agents, retention aids, microparticles, sizing agents and enzymes or their combinations.

According to one embodiment of the invention, the formation of large agglomerates, which settle fast, is monitored and optionally prevented using the monitoring and control system disclosed herein. The most significant factors which contribute to agglomerate formation in paper making processes are dissolved substances in the stream, pH changes, microbes and chemical agents added to the stream, in particular hydrophobation agents. The agglomeration caused by all these sources can be detected and controlled using the present invention. This is because the settling velocity of solid matter is dependent on particle size and therefore also variable in time.

In one embodiment, the modifying agent is added at a rate sufficient to maintain the settling velocity (or mean particle size) below a predetermined level. According to one embodiment, the method is used for controlling the addition rate and/or type of the modifying chemical(s) such that the settling velocity is maintained below 750 NTU/s. In at least some aqueous suspensions of a papermaking process, this corresponds to a mean particle size of solid matter of less than about 20 µm.

Depending on the process or system, settling velocity, settled turbidity or a combination thereof can be used for control purposes. Settled turbidity indicates existence of small particles and their relative amount or level. Settling velocity, on the other hand, indicates existence of agglomerates. Thus, using both these measures provides useful information for process control purposes. By the type and/or amount and/or addition point of the modifying agent(s) the particle size of the solid matter may be affected.

Typically, the average particle size of the modified aqueous stream is preferably kept below 100 µm, in particular below 50 µm, most advantageously below 20 µm. However, in some embodiments the average particle size of the modified aqueous stream is preferably kept below 500 µm, or below 250 µm.

For example, the so-called short circulation of a paper or board machine typically comprises the steps of recovering white water from a wire chest and conveying it back into the process for dilution of the high-consistency fiber-containing pulp fed into the headbox. It is desired to prevent the agglomeration of the solid matter in the circulation stream and thereby prevent or reduce its settling and to be able to get the solid matter back to use. The present invention can be used for achieving this goal.

FIG. 1 shows schematically a paper making process according to one embodiment of the invention. In the process, paper mass is fed to a mixing chest 30 from one or more sources 3, 4, 5. The sources may contain e.g. mechanical, chemical, chemimechanical pulp, recycled fiber and/or broke. One or more chemical modifying agent can be added to each one the masses or to the mixing chest at an addition point 15A. From the mixing chest 30 the mixed mass is conducted to a machine chest 40 in approach flow system in the wet-end. One or more chemicals can be added also in this phase or at the machine chest 40 at an addition points 15B. Further, the treated mass is conducted to the headbox of a paper or board machine 50. Modifying chemicals can be added also at this stage at an addition point 15C.

From a wire section of the paper or board machine 50, white water circulation stream 65 is conducted to a wire pit 60 and circulated back to the headbox. The sampling according to the invention for settling velocity determination is preferably taken from this circulation stream, which is typically used for diluting thick pulp fed into the headbox of the paper or board machine.

According to the embodiment shown in FIG. 1, the sample of the white water circulation stream 65 is conducted to the settling vessel by withdrawing from a sampling point a sidestream 68. The sidestream 68 preferably has a flow rate smaller than the flow rate of the white water circulation stream. The sidestream 68 is conducted to a settling vessel 22.

Alternatively, the side draw can be taken from any other flow (not shown) of the pulp or paper making process. For example, the sampling point can be in the feed line of pulp or broke to a paper or board machine, after one or more chemical addition points. If the sample is taken from a stream containing a high amount of fibres, the sample is preferably filtered and/or screened in order to obtain a substantially fiber-free sample from which the solid particle content is easier to measure.

Figure 1B:
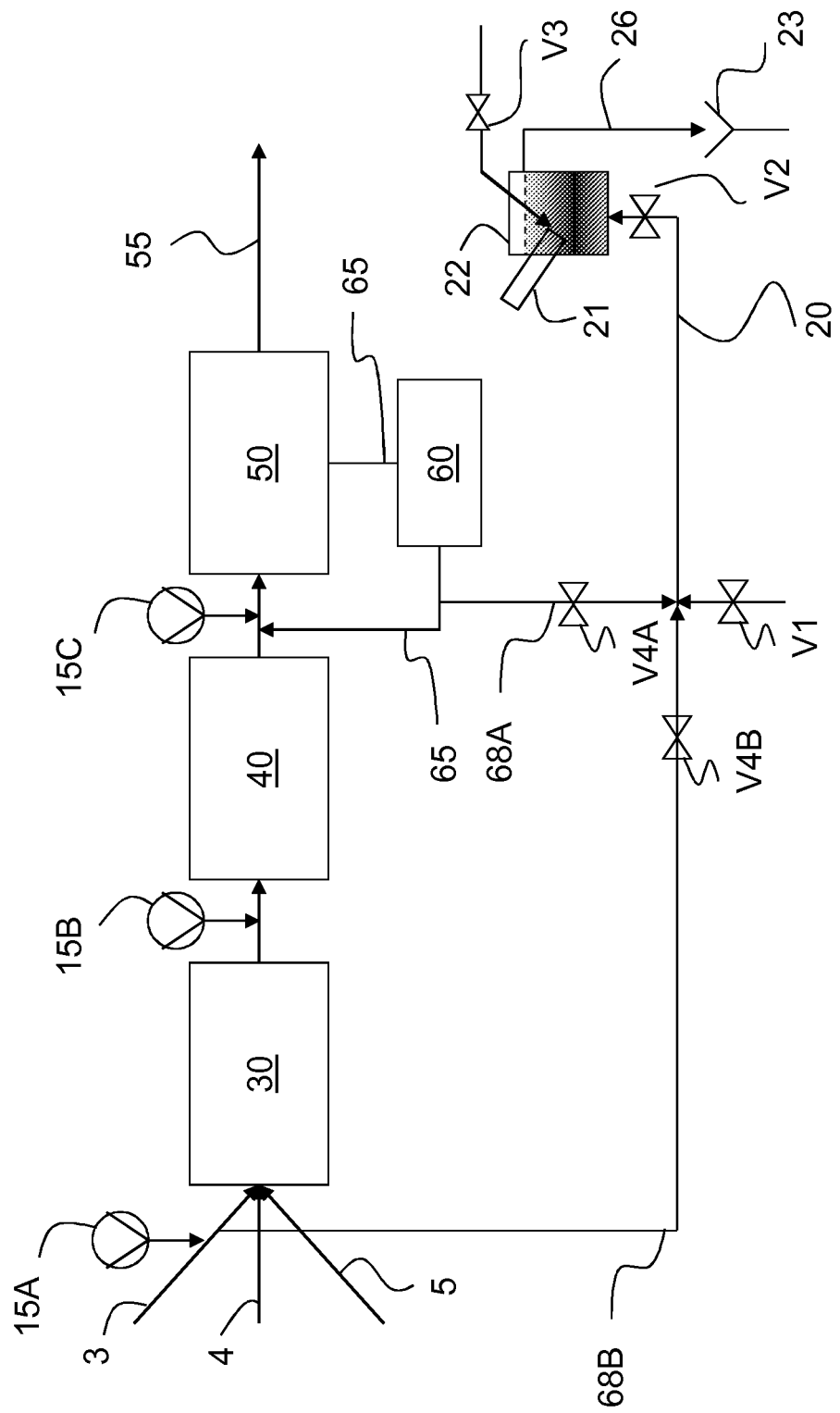
FIG. 1b shows a paper making process with two alternative sampling sidestreams according to another embodiment of the invention.

FIG. 1b shows an embodiment of the process having two alternative sidestreams 68A and 68B, taken from the circulation stream 65 and a process feed line 3, respectively. In addition, there are means, such as valves V4A and V4B arranged in the sidestreams 68A and 68B, respectively, for controlling the source of matter conducted to the settling vessel 22. Accordingly, depending on control, the modified aqueous stream is the white water circulation stream 65 modified at one or more chemical addition points 15A, 15B, 15C or the feed stream 3 modified at the chemical addition point 15A. Thus, the same measurement equipment can be used for monitoring and/or controlling the process at two or more locations or processing stages.

Naturally, as illustrated in FIG. 1b as one example, the system may comprise only one of the various possible sampling points at any of the streams which have been modified with a modifying chemical, i.e. without such source control as illustrated with reference to FIG. 1b.

Preferably, the settling behaviour of the sample is measured using electromagnetic radiation. Thus, the settling vessel 22 comprises detection means 21, such as an optic sensor responsive to solid matter content of the settling vessel in the vicinity of the sensor. The sensor may function in the range of UV, visible or IR wave lengths. As the total solid matter content of the settling vessel does not change, it is preferred to use a sensor capable of local measurement in order to be able to determine the settling velocity conveniently.

An electromagnetic radiation-based detector is preferred over an acoustic detector because it is suitable for low-consistency samples and does not suffer from the problem, of interacting with the sample during the measurement such that it affect the settling properties. For example, the properties of latex particles are temperature-dependent. Electromagnetic radiation is also insensitive to air bubbles or inhomogeneities in the sample, contrary to acoustic waves.

According to one embodiment, the sensor comprises a sensor head allowing for local measurement of solid matter, e.g. in terms of measurement of turbidity or solids content of the sample. The sensor head is positioned at a distance from the bottom of the settling vessel and, optionally, also at a distance from the top of the settling vessel. The sensor head can be directly in the settling vessel or behind a window provided on a wall of the settling vessel. Preferably, the sensor is arranged on a side wall of the settling vessel. The sensor may be arranged at an angle with respect to the side wall.

The settling vessel can be open or closed. Preferably it is of flow-through type, allowing for the settling vessel to be easily connected to a sidestream taken from the modified aqueous stream. Preferably, the sample is conducted to the settling vessel from below.

The sidestream can be interrupted during the turbidity measurement using a valve V2 in the sidestream. An additional washing line with a valve V1 can also be present in the sidedraw channel. The washing line allows for the detector 21 and settling vessel 22 to be washed between successive measurements. The settled sample can be exited from the settling vessel through a purge line 26 and conducted to collector 23 and, optionally circulated back to the process. An additional detector or vessel flush valve V3 and flush line separate from the sidestream channel may also be provided.

The settling velocity is determined by measuring the change of turbidity of the aqueous sidestream. In particular, the change of turbidity or amount of solid substance is measured over a predetermined period of time, preferably in the beginning stage of the settling period, i.e. when there are still large particles settling in the sample, as discussed above.

Figure 2:
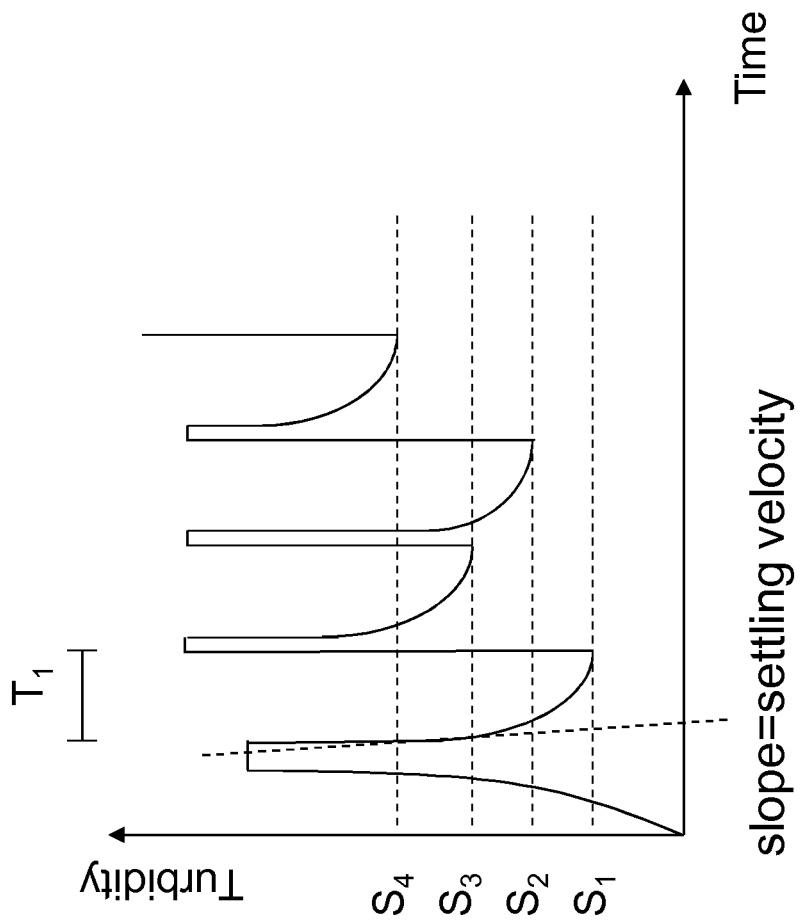
FIG. 2 shows a turbidity vs. time curve in a sequential sampling process according to one embodiment of the invention and the determination of the settling velocity based on the measurement according to one embodiment.

FIG. 2 shows the turbidity vs. time in a settling vessel operated in cyclic manner, each cycle comprising a period of feeding a fresh stream to the settling vessel (sampling, valve V2 open) and a period of settling (measuring and determining the settling velocity, valve V2 closed). The settling period can be generally about 1 to 1200 seconds long or even longer. The settling velocity (slope as dashed line in FIG. 2) is typically determined during the first 1-240, preferably 1-120, seconds, whereas the settled turbidity ($S_1$, $S_2$, $S_3$, $S_4$ in FIG. 2) can be determined after 120-1200 seconds, depending on the properties of the sample. Typically there are 1 to 20 measuring periods/h.

The settling velocity can be determined as an average settling velocity over a period from a predetermined higher turbidity value to a predetermined lower turbidity value, the range corresponding to the desired particle size (e.g. from 700 to 400 NTU) or, alternatively, over a predetermined time period started at a certain moment after the start of the settling period.

The invention claimed is:

1. A method for monitoring settling properties of an aqueous stream online in a pulp, paper or board manufacturing process, the method comprising:
    providing an initial aqueous stream originating from said manufacturing process, wherein the aqueous stream contains solid matter exhibiting a first settling behavior;
    adding a modifying agent to the initial aqueous stream to provide a modified aqueous stream containing solid matter exhibiting a second settling behavior different from the first settling behavior;
    removing a sample from (i) the initial aqueous stream, or modified aqueous stream, (ii) any combination stream comprising the modified aqueous stream, or (iii) any substream of the modified aqueous stream, batchwise, from a sampling point, wherein said sampling point is located in an aqueous circulation stream of a paper or board machine, or in a feed line of pulp or broke to the paper or board machine;
    allowing the sample to settle in the settling vessel and simultaneously measuring the settling velocity of the solid matter in the sample as a function of time,
    wherein the settling velocity of said solid matter is determined by measuring the turbidity of the sample as a function of time; and
    allowing the sample to further settle and after that determining the settled turbidity of the sample;
    based on the determined settling velocity of the solid matter in the sample and the determined settled turbidity of the sample, adding the modifying agent at an addition point of the manufacturing process in an amount that maintains the settling velocity below a predetermined level.

2. The method according to claim 1, wherein said conducting the sample of the initial aqueous stream, or modified aqueous stream, to the settling vessel is performed by withdrawing at the sampling point a sidestream having a flow rate smaller than the flow rate of the aqueous stream, or modified aqueous stream, combination stream, or substream, respectively, and conducting the sidestream to the settling vessel.

3. The method according to claim 2, further comprising the step of interrupting prior to said measurement the sidestream using a valve in said sidestream.

4. The method according to claim 1, wherein the modifying agent comprises coagulants and/or flocculants, passivating chemicals, surfactants, dispersing agents, retention aids, sizing agents, biocides, enzymes or any combination thereof.

5. The method according to claim 1, wherein the solid matter comprises inorganic pigments, fillers and/or precipitates, organic compounds and polymers and biological matter or combinations thereof.

6. The method according to claim 1, wherein said solid matter is present in the sample in suspended and/or colloidal and/or precipitable form.

7. The method according to claim 1, wherein the steps of sampling and measurement of the settling properties of the solid matter in the sample are performed repeatedly in cycles.

8. The method according to claim 7, wherein the cycle is repeated 1 to 20 times/h.

9. The method according to claim 7, wherein the settling velocity is determined based on the settling behavior over a predetermined period starting from a predetermined turbidity value or time after the beginning of the settling, or over an unknown period starting from a predetermined higher turbidity value to a predetermined lower turbidity value.

10. The method according to claim 1, wherein the settling velocity and settled turbidity are used for determining the need of changing the addition rate and/or type of and/or addition point of the modifying agent.

11. The method according to claim 1, wherein the settling velocity and settled turbidity are used for feed forward and/or feedback control of the amount and/or addition point of the modifying agent.

12. The method according to claim 1, wherein the initial aqueous stream contains fibers and the sample is filtered in order to remove fiber material before conducting it to the settling vessel.

13. The method according to claim 1, wherein said sampling point is located in a white water line of a paper machine.

14. The method according to claim 1, wherein the type of modifying agent added is based on the determined settling velocity.

15. The method according to claim 1, wherein the settling velocity is determined from measurements taken within 180 seconds of allowing the sample to settle in the settling vessel.

16. The method according to claim 1, wherein the addition rate of the modifying agent is based on the determined settled turbidity.

17. The method according to claim 14, wherein the addition rate of the modifying agent is based on the determined settled turbidity.

18. The method according to claim 1, wherein the settled turbidity is determined from measurements 5 minutes or more after allowing the sample to settle in the settling vessel.

* * * * *